United States Patent
Kim et al.

(10) Patent No.: US 10,864,146 B2
(45) Date of Patent: *Dec. 15, 2020

(54) MAKEUP COSMETIC COMPOSITION CONTAINING CAPSULES CONTAINING PIGMENTS

(71) Applicant: AMOREPACIFIC CORPORATION, Seoul (KR)

(72) Inventors: Eun Jeong Kim, Yongin-si (KR); Min Kyung Shim, Yongin-si (KR); Yan Li, Yongin-si (KR); Hyun Suk Lee, Yongin-si (KR); Sun Kyung Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/338,380

(22) PCT Filed: Sep. 29, 2017

(86) PCT No.: PCT/KR2017/010919
§ 371 (c)(1),
(2) Date: Mar. 29, 2019

(87) PCT Pub. No.: WO2018/062932
PCT Pub. Date: Apr. 5, 2018

(65) Prior Publication Data
US 2020/0022887 A1    Jan. 23, 2020

(30) Foreign Application Priority Data

Sep. 30, 2016  (KR) .................. 10-2016-0126881
Sep. 28, 2017  (KR) .................. 10-2017-0126138

(51) Int. Cl.
*A61K 8/49* (2006.01)
*A61K 8/81* (2006.01)
(Continued)

(52) U.S. Cl.
CPC .................. *A61K 8/11* (2013.01); *A61K 8/04* (2013.01); *A61K 8/25* (2013.01); *A61K 8/29* (2013.01);
(Continued)

(58) Field of Classification Search
None
See application file for complete search history.

(56) References Cited

U.S. PATENT DOCUMENTS

2005/0069704 A1 *  3/2005  Rathschlag ......... C09B 67/0004
                                                                428/402.21
2014/0356403 A1   12/2014  Zhu et al.
(Continued)

FOREIGN PATENT DOCUMENTS

CN    104418972 A    3/2015
EP    2 939 653 A1   11/2015
(Continued)

OTHER PUBLICATIONS

International Search Report for PCT/KR2017/010919 dated Jan. 15, 2018 (PCT/ISA/210).
(Continued)

*Primary Examiner* — Kyung S Chang
(74) *Attorney, Agent, or Firm* — Sughrue Mion, PLLC (57) ABSTRACT

The present invention relates to a makeup cosmetic composition containing capsules containing pigments in an inner layer thereof and, more specifically, to a makeup cosmetic composition, which contains a pigment in an inner layer and blocks a pigment from an external environment, thereby preventing pigment discoloration caused by the external
(Continued)

environment, and contains capsules readily broken so as to enable color to show when applied to the skin, thereby showing color when applied to the skin even though the color of a formulation is nearly colorless and having an excellent skin coloring ability.

4 Claims, 7 Drawing Sheets
(7 of 7 Drawing Sheet(s) Filed in Color)

(51) Int. Cl.
    *A61K 8/365* (2006.01)
    *A61K 8/11* (2006.01)
    *A61K 8/25* (2006.01)
    *A61K 8/04* (2006.01)
    *A61Q 1/06* (2006.01)
    *A61K 8/29* (2006.01)
    *A61K 8/362* (2006.01)
    *A61Q 1/08* (2006.01)
    *A61K 8/34* (2006.01)

(52) U.S. Cl.
    CPC .............. *A61K 8/345* (2013.01); *A61K 8/362* (2013.01); *A61Q 1/06* (2013.01); *A61Q 1/08* (2013.01); *A61K 2800/43* (2013.01); *A61K 2800/56* (2013.01)

(56) References Cited

U.S. PATENT DOCUMENTS

2016/0170091 A1   6/2016   Li et al.
2016/0367449 A1  12/2016  Son et al.
2020/0022887 A1   1/2020   Kim et al.

FOREIGN PATENT DOCUMENTS

| KR | 10-2013-0079244 A | 7/2013 |
| KR | 10-1342958 B1 | 12/2013 |
| KR | 10-2014-0113728 A | 9/2014 |
| WO | 01/49817 A2 | 7/2001 |
| WO | 03/037995 A1 | 5/2003 |
| WO | 2015/044306 A1 | 4/2015 |
| WO | 2015/166459 A1 | 11/2015 |
| WO | 2017/085446 A1 | 5/2017 |

OTHER PUBLICATIONS

Schilling et al., "Citric acid as a solid-state plasticizer for Eudragit RS PO", Journal of Pharmacy and Pharmacology, 2007, vol. 59, pp. 1493-1500 (8 pages total).
International Searching Authority, International Search Report dated Jan. 31, 2018, issued in application No. PCT/KR2017/010589.

* cited by examiner

[FIG. 1]

|  | Comparative Formulation Example 1 | Comparative Formulation Example 2 | Formulation Example |
|---|---|---|---|
| Stick appearance color | | | |
| Skin coloring ability | | | |

[FIG. 2]

[Formulation Example 2]     [Comparative Formulation Example 3]

[FIG. 3]

| Type | containing non-encapsulated pigment | containing pigment'capsule | Improvement of appearance (△E) |
|---|---|---|---|
| Red 27 |  |  | 14.92 --> 9.33 |

MAKEUP COSMETIC COMPOSITION CONTAINING CAPSULES CONTAINING PIGMENTS

CROSS REFERENCE TO RELATED APPLICATIONS

This application is a National Stage of International Application No. PCT/KR2017/010919 filed Sep. 29, 2017, claiming priority based on Korean patent Application No. 10-2016-0126881, filed Sep. 30, 2016 and Korean Patent Application No. 10-2017-0126138, filed Sep. 28, 2017.

TECHNICAL FIELD

The present invention relates to a makeup cosmetic composition containing capsules containing pigments in an inner layer thereof and, more specifically, to a makeup cosmetic composition, which contains a pigment in an inner layer and blocks a pigment from an external environment, thereby preventing pigment discoloration caused by the external environment, and contains capsules readily cracked or broken so as to enable color to show when applied to skin, thereby showing color when applied to the skin even though the color of a formulation is nearly colorless and having an excellent skin coloring ability.

BACKGROUND ART

In general, organic pigments often used in cosmetics are very poor in dispersibility in oil dispersion makeup formulations. The water-soluble pigment naturally sinks without being uniformly mixed in an oily dispersion. Similarly, in the case of bromo pigments, which are widely used as oil-soluble pigments, the difference in solubility according to oil is large, and the color to developed is also greatly different. Due to these problems, when organic pigments are applied to cosmetics, the pigment particles may not be easily dissolved, and particles may be apparently seen in many cases. In particular, when the applied to skin, the color of the contents is clearly expressed, thereby adversely affecting the appearance.

Therefore, in order to realize a technique in which the organic pigment is uniformly dispersed in the oil phase dispersion and the color can be uniformly expressed, there is a need for a technology for finely dispersing the pigment particles, and ensuring encapsulation for stable dispersion as well as proper cracking or breaking for color development.

DETAILED DESCRIPTION OF THE INVENTION

Technical Problem

The present inventors have prepared a pigment capsule containing a pigment, wherein the capsule has an inner layer (inside) in which silica, a pigment, and a titanium dioxide pigment are dispersed, and an outer layer covered with a polymer binder having a glass transition temperature of 130° C. or higher, and have found that the capsules effectively protect the pigment from the external environment while allowing the pigment to be uniformly dispersed in an oily dispersion, and is easily cracked or broken even with a small force, and the pigment in the inner layer of the capsule develops color when applied to skin, and has excellent adherence to skin, thereby completing the present invention.

Accordingly, it is an object of the present invention to provide a makeup cosmetic composition containing a capsule structure containing a pigment, which protects the pigment from the external environment and secures the stability of the pigment and dispersibility of the pigment.

Technical Solution

In order to achieve the object above, one aspect of the present disclosure provides a makeup cosmetic composition containing a pigment capsule, wherein the capsule has an inner layer in which silica, a pigment and a titanium dioxide pigment are dispersed, and an exterior covered with a polymer binder having a glass transition temperature of 130° C. or higher, and wherein a $C_3$-$C_9$ trivalent carboxylic acid is contained in the inner layer of the capsule.

Advantageous Effects

The capsule contained the makeup cosmetic composition of the present invention can solve the problem related to instability of the pigment against the external environment by completely blocking the pigment from the external environment, while improving the dispersibility in the oil phase of pigments, and also, the capsule is stable during the formulation process, but when applied to the skin, it is easily cracked or broken by force applied while rubbing or scrubbing with a hand or a tool, thereby causing color development easily.

Further, the color development of the pigment is blocked and thus the color due to pigment does not appear in the product, but the color development occurs after the capsule is applied to skin, which may arouse users' interests when using the product.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

The present invention provides a makeup cosmetic composition containing a pigment capsule, wherein an inner layer of the pigment capsule is dispersed with silica, a pigment and a titanium dioxide pigment, and an outer layer of the capsule is covered with a polymer binder having a glass transition temperature of 130° C. or higher.

Specifically, the pigment capsule used in the present invention is a capsule containing a pigment, wherein an inner layer of the capsule is dispersed with silica, a pigment and a titanium dioxide pigment, an outer layer of the capsule is covered with a polymer binder having a glass transition temperature of 130° C. or higher, and a $C_3$-$C_9$ trivalent carboxylic acid is contained in the inner layer of the capsule.

The makeup cosmetic composition according to the present invention contains the above-mentioned pigment capsule in an amount of 0.01 to 30% by weight based on the total weight of the composition. When the content is less than 0.01% by weight, the coloring effect on the skin is small, and when the content is more than 30% by weight, the coloring effect is too large and thus it is expressed in an unnatural color and the feeling of use is also deteriorated.

Furthermore, in order to mask the color of the pigment capsule to make the appearance color of the formulation closer to colorless, the makeup cosmetic composition according to the present invention may further include polyhydroxy stearate, dipentaerythrityl tetrabehenate/polyhydroxy stearate, dipentaerythrityl tri-polyhydroxystearate, ethylhexyl polyhydroxystearate, iso-octyl polyhydroxystearate, pentaerythrityl behenate/polyhydroxystearate, and the like. By including this, the color of the pigment can be suppressed from being expressed before applying to skin, and the stability of the pigment capsule can be enhanced. The content thereof is preferably 0.01 to 40% by weight, more preferably 3 to 40% by weight based on the total weight of the composition. When the content is less than 0.01% by weight, mixing with the pigment capsules is not performed well and the purpose of trying to make the appearance color brighter is not achieved. When the content is more than 40% by weight, the pigment dispersibility of various pigments contained in the formulation is poor, and thus an aggregation phenomenon for each pigment occurs or it is difficult to control the feeling of use.

In the pigment capsule used in the present invention, the instability of the pigment due to changes in the external environment can be solved, and the degree of change of color developed according to the oil contained in the formulation to disperse the pigment capsules, various additives, the change in the pH of the formulation, and the like, is not large, so that the color of the pigment can be expressed at a constant level regardless of the external environment.

The pigment capsule used in the present invention is characterized by having physical properties of improving the dispersibility of pigments in an oily dispersion and maintaining the stability during formulation or storage of the formulated product, but being cracked or broken by the pressure at the moment of application to the skin.

The pigment capsule of the present invention has an average diameter of 10 to 15 μm, preferably 10 to 12 μm, and the pigment capsule according to the present invention may be easily cracked or broken, ruptured, dissolved or disintegrated by a small pressure, that is, the pressure generally applied when pressed, rubbed, wiped or scrubbed with a hand or a tool (cotton cloth, sponge, brush, etc.).

In the present invention, in particular, fumed silica (silica dimethyl silylate) is used as the silica.

In addition, in order to increase the hardness of the capsule for the purpose of completely blocking the pigment from the external environment and securing physical stability thereof, by using a polymer binder, the present invention provides a capsule in which a pigment and silica are dispersed in the inner layer, and a barrier membrane from the exterior is formed by the polymer binder.

In many cases, a makeup cosmetic composition is subjected to a high temperature during the formulation process, and in particular, a composition for lip makeup such as lipstick is mainly formulated at a high temperature (for example, 95° C. or higher) due to the nature of the mixing process of raw materials, and thus it is very important to secure thermal stability of the capsule. Therefore, as a polymer binder in the present invention, those having a glass transition temperature (Tg) of 130° C. or higher are used.

In addition, the purpose of the pigment capsule in the present invention is that discoloration of the pigment in the capsule does not occur until the product is applied by a user, and thus, the discoloration of the pigment should not occur due to the polymer used.

Therefore, the polymer binder used in the present invention may be those that do not cause discoloration of the pigment, while having a high glass transition temperature (130° C. or higher). In order to satisfy such a condition, an acrylate copolymer, in particular, a polymethacrylate-based copolymer, is used in the present invention, preferably acrylic acid and acrylate copolymer, more preferably acrylic acid and methacrylate copolymer, and in particular, methacrylic acid and methacrylate copolymer are used.

The polymer binder used in the present invention may be used up to 90% by weight based on the total weight of the capsule. However, when the polymer binder is used in an excessive amount, the contents of silica, titanium dioxide, and pigment become relatively small, so that the shape of the capsule may not be spherical and become distorted, and it may not crack or break when rubbed by a hand. Therefore, in consideration of these factors, the content of the polymer binder is preferably 5 to 20% by weight, more preferably 10 to 20% by weight based on the total weight of the capsule.

The pigment used in the present invention is not particularly limited by its type, such as water-soluble pigments and oil-soluble pigments. And the oil-soluble pigments are preferred.

For example, the following pigments may be used.

organic dyes such as azo-based, anthraquinone-based, indigo-based, xanthene-based, pyrene-based, quinoline-based, triphenylmethane-based, fluorane dyes; and insoluble salts of sodium, potassium, calcium, barium, aluminum, zirconium, strontium, titanium of acid-based dyes such as azo-based, anthraquinone-based, indigo-based, xanthene-based, pyrene-based, quinoline-based, triphenylmethane-based, fluorane dyes, and these dyes may include at least one carboxylic or sulfonic acid group.

As specific examples of organic dyes, those having the following trade names may be mentioned:

D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No.

7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

As the pigment capsule according to the present invention, particularly, a pigment such as oil-soluble pigment Red 27, which exhibits a difference in color expression under humidity changes and alkaline conditions, thus having poor stability, may also be used.

Red 27 is a bromo-oil-soluble pigment, which is a magic pigment that exhibits the difference in color expression under humidity changes and alkaline conditions. However, when this is directly incorporated into a makeup cosmetic composition, particularly a lipstick, the color changes rapidly depending on the pH of the raw material contained in the lipstick, etc. and thus in order to achieve the desired color, formulation configurations are very limited. In addition, Red 27 has a different solubility for each oil, and thus, if it is not dissolved well, it may appear like an undissolved red pigment impurity. Further, when applied to a lip, the surface making a contact with the lip is often changed reddish due to the moisture of the lip and is often not good in appearance. There are many obstacles in the development of the product because the color deviation is severe according to the production conditions even during the production.

However, when a pigment having poor stability is supported on the capsule and placed in the composition to prepare the desired product, the existing problems can be greatly improved.

In the pigment capsule of the present invention, the pigment may be used up to 90% by weight based on the total weight of the capsule. However, when the pigment is used in an excessive amount, the contents of the polymer binder forming the capsule outer layer become relatively small, and thus, the pigment cannot be completely protected from the external environment, thereby causing a problem in stability of the pigment. Therefore, in consideration of these factors, the content of the pigment may be preferably 0.00001 to 50% by weight, preferably 10 to 50% by weight based on the total weight of the capsule.

Further, the pigment capsule of the present invention contains a $C_3$-$C_9$ trivalent carboxylic acid, preferably, citric acid, propionic acid, iso-citric acid, aconitic acid, tricarballylic acid, and trimesic acid in the inner layer. By containing a $C_3$-$C_9$ trivalent carboxylic acid, the pH of the capsule interior can be maintained under an acidic condition, thereby preventing discoloration of the pigment due to contact with an alkali oil. At this time, the content of the $C_3$-$C_9$ trivalent carboxylic acid is not particularly limited as long as it prevents discoloration of the pigment and thereby does not alter the exterior color of the capsule, and in particular, when formulated into a cosmetic composition for lip makeup, as long as it is suitable for the pH standard of the composition. Preferably, it may be added in an amount of 1 to 20% by weight, preferably 1 to 5% by weight based on the total weight of the capsule. When the amount is less than 1% by weight, it may be insufficient to prevent the discoloration of the pigment, and when the amount is more than 20% by weight, the difference in the effects due to an increase in the content is insignificant.

The present invention provides a method for producing a pigment capsule including a pigment, the method including the steps of:

1) dissolving a polymer binder and a $C_3$-$C_9$ trivalent carboxylic acid in a first solvent and dissolving a pigment in a second solvent, respectively, and then mixing them to allow the pigment to disperse in the polymer binder solution;

2) adding silica and titanium dioxide to the mixed polymer solution in which the pigment is dispersed, and dispersing the mixture;

3) spray drying the solution obtained in step 2); and 4) obtaining spray-dried pigment/polymer binder composite powder particles.

In the present invention, in order to improve the stability and the effect of the pigment capsule, the pigment is first dispersed in a specific oil, thereby suppressing the color development before applying to skin, and enhancing the stability of capsule.

Specifically, in the method of the present invention, the step of dissolving a polymer binder and a pigment is characterized by dissolving each of the polymer binder and the pigment in different solvents so that the both can be sufficiently, completely dissolved, preferably to the extent of 100%, and then mixing and using them, while preventing color development of the pigment.

As the polymer binder and pigment used in the present invention, those described above can be used.

As the solvent for dissolving the polymer binder, an organic solvent, preferably, at least one organic solvent selected from the group consisting of a $C_1$-$C_4$ lower alcohol (for example, methanol, ethanol, isopropanol, butanol, etc.), acetone, and a mixture thereof, or a mixture of the organic solvent and water, for example, methanol, methanol/water (97:3), ethanol, ethanol/water (6:4), isopropanol, isopropanol/water (97:3), isopropanol/water (6:4), N-butanol, acetone, acetone/water (97:3), acetone/water (6:4), acetone/isopropanol (4:6) may be used, more preferably, ethanol or acetone may be used.

Further, as the solvent for dissolving the pigment, a chlorine-containing hydrocarbon-based organic solvent, preferably chloroform, dichloromethane (DCM), and more preferably dichloromethane (DCM) may be used.

In the method of the present invention, the ratio of the solvent for dissolving the polymer binder to the solvent for dissolving the pigment is about 3:7 by volume. When the ratio of the solvent is less than about 3:7 (for example, 1:9, 2:8, etc.), the polymer binder may be precipitated, and when the ratio of the solvent is greater than about 3:7, (for example, 4:6, 5:5, 9:1, etc.), discoloration of the pigment may occur, which is not preferred.

When the polymer binder is dissolved in a solvent, the $C_3$-$C_9$ trivalent carboxylic acid, preferably, citric acid, propionic acid, or tricarballylic acid may be added thereto. By containing the $C_3$-$C_9$ trivalent carboxylic acid, the pH of the capsule inner layer can be maintained under an acidic condition, thereby preventing discoloration of the pigment due to contact with an alkali oil. At this time, the content of the $C_3$-$C_9$ trivalent carboxylic acid is not particularly limited as long as it prevents discoloration of the pigment and thereby does not alter the exterior color of the capsule, and may be preferably contained in an amount of 1 to 20% by weight based on the total weight of the capsule. When the amount is less than 1% by weight, it may be insufficient to prevent the discoloration of the pigment, and when the amount of more than 20% by weight, the difference in the effects due to an increase in the content is insignificant.

Spray drying may be carried out under the following conditions: Feed rate—amount of air fed to twin-fluid nozzle: 40 L/min, amount of dispersion fed: 100 g/min; Environmental conditions—temperature of dispersion (reaction solution): 25° C., spray dryer inlet temperature: 80° C., spray dryer outlet temperature: 60° C. At this time, spray drying may be performed while stirring the mixed polymer solution continuously through a stirrer.

The pigment capsule prepared according to the present invention isolates the pigment from the external environment and does not cause color development of the pigment before application of the final product, for example, cosmetics, to the skin, and also, it contains titanium dioxide pigment in the pigment capsule to mask the inherent color of the pigment, thereby rendering the color of the formulation itself to become close to colorless. That is, it causes color development when the product which is close to colorless, is applied to the skin, and thus, it is also possible to increase interest and attention during make-up.

The composition of the present invention is not particularly limited in its formulation, but it can be applied to all formulations with oil, such as oil dispersion lipstick, oil dispersion liquid rouge, oil dispersion lip balm, oil dispersion lip gloss, oil dispersion lip palette, stick blusher, powder blusher, stick shadow, powder shadow, emulsion type lipstick, emulsion type liquid rouge, emulsion type stick lip balm, etc.

MODE FOR CARRYING OUT THE INVENTION

Hereinafter, the constitutions and effects of the present invention will be described in detail by way of Examples and Test Examples shown below. However, these Examples and Test Examples are given for illustrative purposes only to help understanding of the present invention, and the scope of the invention is not intended to be limited to or by these Examples and Test Examples.

[Example 1] Preparation of Pigment Capsule (1)

Red 27 Lake (20 g, 10%) was dispersed in dichloromethane (DCM, 1580 mL). Citric acid (10 g, 5%) was dissolved in ethanol (402 mL) heated to 60° C., and then an acrylate copolymer as a polymer binder (Eudragit® L 100, manufactured by Evonik Degussa; 20 g, 10%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or less and mixed with the Red 27 Lake solution. At this time, the volume ratio of ethanol and dichloromethane is 3:7. Then, silica (AEROSIL® R972, manufactured by Evonik Degussa; 140 g, 70%) and TiO$_2$ (Purolan® E 171A, manufactured by LANXESS; 10 g, 5%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITUTE, capacity: 10 kg/hr (H$_2$O basis)) and encapsulated.

[Example 2] Preparation of Pigment Capsule (2)

Red 27 Lake (60 g, 30%) was dispersed in dichloromethane (DCM, 1580 mL). Citric acid (10 g, 5%) was dissolved in ethanol (402 mL) heated to 60° C., and then an acrylate copolymer as a polymer binder (Eudragit® L 100, manufactured by Evonik Degussa; 20 g, 10%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or less and mixed with the Red 27 Lake solution. Then, silica (AEROSIL® R972, manufactured by Evonik Degussa; 100 g, 50%) and TiO$_2$ (Purolan® E 171A, manufactured by LANXESS; 10 g, 5%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITUTE, capacity: 10 kg/hr (H$_2$O basis)) and encapsulated.

[Example 3] Preparation of Pigment Capsule (3)

Red 27 Lake (60 g, 30%) was dispersed in dichloromethane (DCM, 1580 mL). Citric acid (15 g, 7.5%) was dissolved in ethanol (402 mL) heated to 60° C., and then an acrylate copolymer as a polymer binder (Eudragit® L 100, manufactured by Evonik Degussa; 30 g, 15%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or below and mixed with the Red 27 Lake solution. Then, silica (AEROSIL® R972, manufactured by Evonik Degussa; 70 g, 35%) and TiO$_2$ (Purolan® E 171A, manufactured by LANXESS; 25 g, 12.5%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITUTE, capacity: 10 kg/hr (H$_2$O basis)) and encapsulated.

[Example 4] Preparation of Pigment Capsule (4)

Red 27 Lake (40 g, 20%) was dispersed in dichloromethane (DCM, 1580 mL). Citric acid (10 g, 5%) was dissolved in ethanol (402 mL) heated to 60° C., and then an acrylate copolymer as a polymer binder (Eudragit® L 100, manufactured by Evonik Degussa; 30 g, 15%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or below and mixed with the Red 27 Lake solution. Then, silica (AEROSIL® R972, manufactured by Evonik Degussa; 100 g, 50%) and TiO$_2$ (Purolan® E 171A, manufactured by LANXESS; 20 g, 10%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITUTE, capacity: 10 kg/hr (H$_2$O basis)) and encapsulated.

[Example 5] Preparation of Pigment Capsule (5)

Red 27 Lake (40 g, 20%) was dispersed in dichloromethane (DCM, 1580 mL). Citric acid (15 g, 7.5%) was dissolved in ethanol (402 mL) heated to 60° C., and then an acrylate copolymer as a polymer binder (Eudragit® L 100, manufactured by Evonik Degussa; 30 g, 15%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or below and mixed with the Red 27 Lake solution. Then, silica (AEROSIL® R972, manufactured by Evonik Degussa; 85 g, 42.5%) and $TiO_2$ (Purolan® E 171A, manufactured by LANXESS; 30 g, 15%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITUTE, capacity: 10 kg/hr ($H_2O$ basis)) and encapsulated.

[Comparative Example 1] Preparation of Pigment Capsule

A composite powder particle containing a pigment was obtained in the same manner as in Example 1 except that polyvinyl pyrrolidone was used as the polymer binder (pigment content: 10%).

[Test Example 1] Comparison of Appearance and Coloring Ability of the Formulation (Lipstick)

An oil dispersion type lipstick containing the capsules of Example 1 and Comparative Example 1 and having the composition of Table 1 below was prepared according to a conventional lipstick manufacturing method.

TABLE 1

(unit: wt %)

|  | Formulation Example 1 | Comparative Formulation Example 1 | Comparative Formulation Example 2 |
|---|---|---|---|
| Polyethylene | 15.0 | 15.0 | 15.0 |
| Distearyl malate | 30.0 | 30.0 | 30.0 |
| Vaseline | 20.0 | 20.0 | 20.0 |
| Caprylic/capric triglyceride | 15.0 | 15.0 | 15.0 |
| Red 27 | — | 0.1 | — |
| Capsule of Example 1 | 1.0 | — | — |
| Capsule of Comparative Example 1 | — | — | 1.0 |

In the oil dispersion lipstick formulations prepared, the pigment dispersibility, the surface state of the stick (whether or not the pigment grains can be seen on the surface of the stick), the color of the raw material capsule, the stick appearance color and the skin coloring ability were evaluated, and the evaluation results are shown in Table 2 and FIG. 1 below.

TABLE 2

|  | Formulation Example 1 | Comparative Formulation Example 1 | Comparative Formulation Example 2 |
|---|---|---|---|
| Dispersibility | ○ | Δ | ○ |
| Stick surface state | ◉ | X | ○ |
| Raw material(capsule) color | Pale pink | Pale pink | Dark pink |
| Stick appearance color | Very pale pink | Red | Red |
| Skin coloring ability | ◉ | ◉ | Δ |

(X: bad, Δ: normal, ○: good, ◉: excellent)

Figure 1:
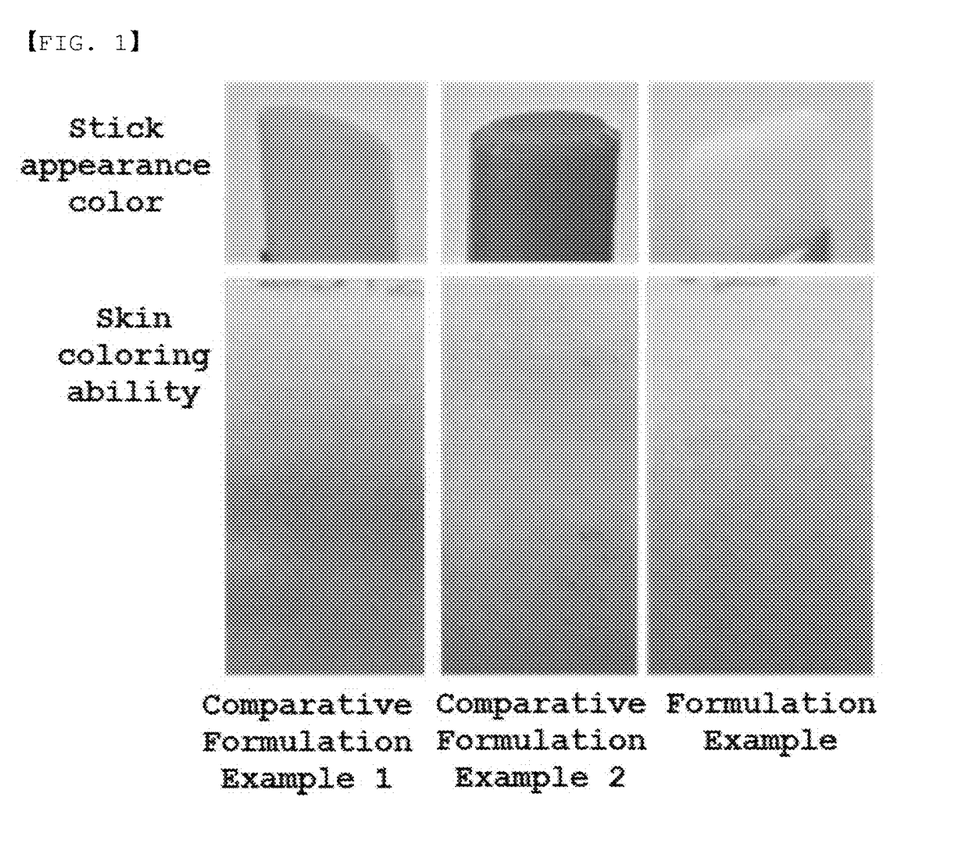
FIG. 1 shows the appearance color and skin coloring ability of lipstick prepared according to the present invention.

From the results shown in Table 2 and FIG. 1, it can be seen that Comparative Formulation Example 1 not containing a capsule is discolored after color development occurs in the process of formulation and thus the stick appearance shows a pale pink, and that in Comparative Formulation Example 2, the pigment is supported on the capsules, but discoloration of the pigment is caused by the polymer binder (polyvinylpyrrolidone), and the color of the capsule becomes dark pink, and the stick appearance also shows a dark pink color, but when applied to skin, the coloring ability is rather reduced.

On the other hand, in the case of Formulation Example 1 to which the capsule of Example 1 is applied, the dispersibility of the pigment is excellent and thus no pigment granules are shown on the surface of the stick, and the stick appearance color shows a very pale pink color close to colorless, but when applied to skin, it is colored well in red.

[Test Example 2] Comparison of Appearance and Coloring Ability of Formulation (Lipstick)

An oil-dispersion type lipstick including the capsule of Example 1 and having the composition shown in Table 3 below was prepared according to a conventional lipstick manufacturing method.

TABLE 3

|  | Formulation 2 | Comparative Formulation 3 | Comparative Formulation 4 | Comparative Formulation 5 |
|---|---|---|---|---|
| Polyethylene | 15.0 | 15.0 | 15.0 | 15.0 |
| Distearyl malate | 49.0 | 54.0 | 4.0 | 53.0 |
| Vaseline | 20.0 | 20.0 | 20.0 | 20.0 |
| Caprylic/capric triglyceride | 10.0 | 10.0 | 10.0 | 10.0 |
| Capsule of Example 1 | 1.0 | 1.0 | 1.0 | 1.0 |
| Dipentaerythrityl tri-polyhydroxystearate | 5.0 | — | 50.0 | 1.0 |

Preparation Method

Predetermined contents of the capsules of Example 1 and dipentaerythrityl tri-polyhydroxy stearate were mixed, and then dispersed with an Agi mixer for 5 minutes. It was added to other lipstick contents dissolved at 90° C. and dispersed with a homogenizer for 10 minutes.

Figure 2:
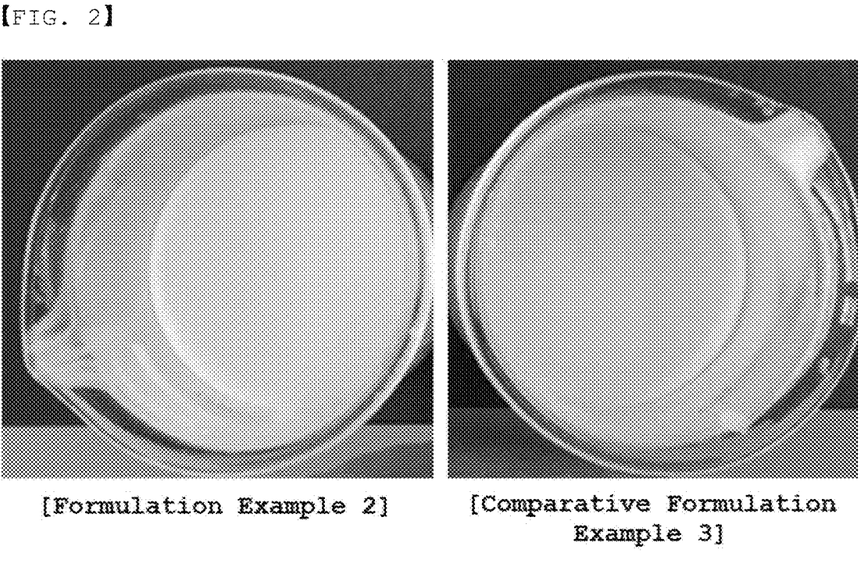
FIG. 2 shows the appearance color in a composition further containing dipentaerythrityl tri-polyhydroxystearate.

In the prepared formulation, the appearance color brightness, the skin coloring ability and the pigment dispersibility were evaluated, and the evaluation results are shown in Table 4 and FIG. 2 (the state before the formulation was dispersed and solidified).

TABLE 4

|  | Formulation 2 | Comparative Formulation 3 | Comparative Formulation 4 | Comparative Formulation 5 |
|---|---|---|---|---|
| Appearance color brightness | ⊚ | ○ | ⊚⊚ | ○ |
| Skin coloring ability | ⊚ | ⊚ | ⊚ | ⊚ |
| Pigment dispersibility | ⊚ | ⊚ | X | ○ |

(X; bad, Δ: normal, ○; good, ⊚: excellent, ⊚⊚: very excellent)

Looking at the state of the stick surface after applying to a lip, it can be confirmed that in the case of Formulation Example 2 using a mixture of dipentaerythrityl tri-polyhydroxy stearate and capsule, the appearance is less red and the color of the formulation is brighter, compared to Comparative Formulation Example 3 not containing dipentaerythrityl tri-polyhydroxy stearate. However, if the content of dipentaerythrityl tri-polyhydroxystearate reaches 50% by weight (Comparative Formulation Example 4), the appearance color of the formulation becomes brighter, but the pigment dispersibility is not good, and thus the aggregation phenomenon occurs by pigment. On the other hand, if the content of dipentaerythrityl tri-polyhydroxystearate is less than 3% by weight (Comparative Formulation Example 5), it has been found that the pigment and the dipentaerythrityl tri-polyhydroxystearate are not mixed evenly and the pigment present in the powder phase was increased, so that the effect of improving the appearance brightness is small and the pigment dispersibility is not good.

[Test Example 3] Observation of Color Stability According to the Change of pH

When the pigment capsule according to the present invention was contained, the compositions were prepared with the compositions shown in Table 5 below, in order to observe the color stability according to the pH. At this time, since it is advantageous to check the change in color under conditions in which red/yellow/white are mixed together, rather than single tone color conditions, yellow YELLOW 10 LAKE, and white titanium dioxide were blended with a red pigment, Red 27.

Figure 3:
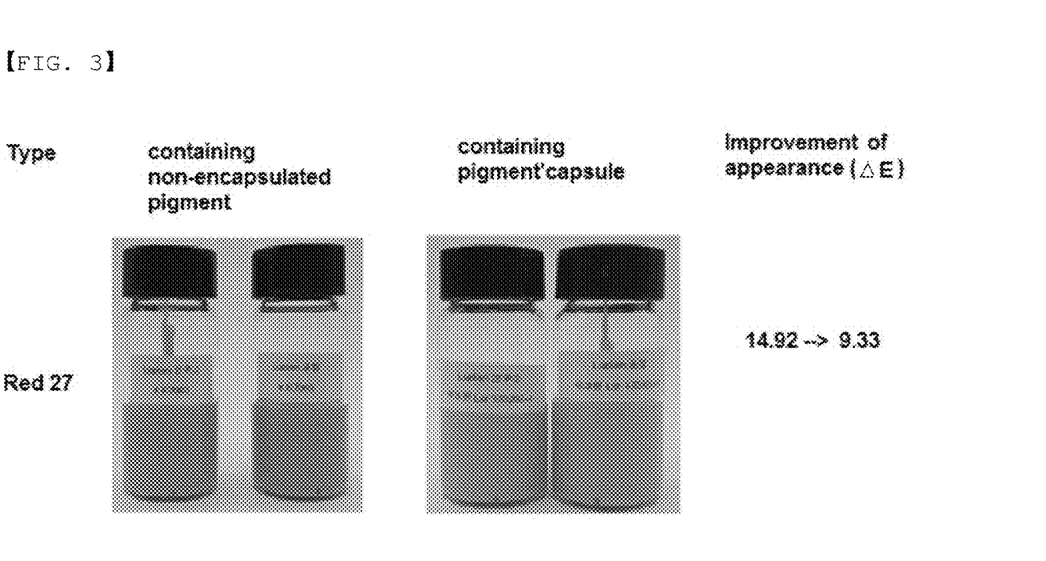
FIG. 3 shows the degree of color change depending on the pH of a composition comprising a pigment capsule or a non-encapsulated pigment.

Formulation (i) and Formulation (iii) were prepared with phytosteryl isostearyl dimer dilinoleate having a pH of 7.5, and Formulation (ii) and Formulation (iv) were prepared with phytosteryl isostearyl dimer dilinoleate having a pH of 7.7. First, 10 g of phytosteryl isostearyl dimer dilinoleate (LUSPLAN PI-DA) was heated to 95° C. or higher, and then a non-encapsulated pigment (Red 27 Lake) (0.01 g) or an encapsulated pigment (Red 27 Lake) (0.1 g) was mixed, to which 0.6 g of titanium dioxide and 0.3 g of yellow pigment (YELLOW 10 LAKE) were added and mixed well. Thereafter, the appearance color of the solution was observed, and the results are shown in Table 5 and FIG. 3 below. Here, the degree of change in appearance color was indicated by the ΔE value, and the ΔE value can be obtained from the color coordinates L, a and b values according to the following Equation 1. It means that the smaller the value, the smaller the degree of change in color.

$$\Delta E((dL)^2+(da)^2+(db)^2))^{1/2} \quad \text{[Equation 1]}$$

TABLE 5

(unit: wt %)

| | Raw material | Formulation (i) | Formulation (ii) | Formulation (iii) | Formulation (iv) |
|---|---|---|---|---|---|
| Oil | phytosteryl isostearyl dimer | 10 | 10 | 10 | 10 |
| Pigment | titanium dioxide (CI 77891) | 0.36 | 0.36 | 0.36 | 0.36 |
| Dye | YELLOW 10 LAKE (CI 47005) | 0.12 | 0.12 | 0.12 | 0.12 |
| Dye | Non-encapsulated pigment (Red 27) | 0.01 | 0.01 | — | — |
| | Pigment capsule (Red 27) | — | — | 0.1 | 0.1 |

Referring to Table 5 and FIG. 3, it can be confirmed that blending the pigment capsules reduces the color change by pH by about 30% (ΔE standard), rather than directly blending the non-encapsulated pigment. This is believed to be due to less influence of the pH in the formulation by the citric acid used in the encapsulation in the case of pigment capsules.

[Test Example 4] Observation of Expression of Appearance Color of Capsules According to Content of Citric Acid Lipstick formulations containing the pigment capsules according to the present invention were prepared with the compositions of Table 6 below. Formulation (a) contains the capsule of Example 4, Formulation (b) contains the capsule of Example 5, Formulation (c) contains the capsule of Example 6, and Formulation (d) contains the capsule of Example 7.

TABLE 6

(unit: wt %)

| | Formulation (a) | Formulation (b) | Formulation (c) | Formulation (d) |
|---|---|---|---|---|
| Polyethylene | 15.0 | 15.0 | 15.0 | 15.0 |
| Distearyl malate | 30.0 | 30.0 | 30.0 | 30.0 |
| Vaseline | 20.0 | 20.0 | 20.0 | 20.0 |
| Caprylic/capric triglyceride | 15.0 | 15.0 | 15.0 | 15.0 |
| Red 27 | 0.1 | — | — | — |
| Capsule | — | 1.0 | 1.0 | 1.0 |

The appearance of the lipstick formulations prepared with the above compositions was observed, and the degree of change of appearance color according to the content of citric acid was observed. The results are shown in FIG. 3.

Figure 4:
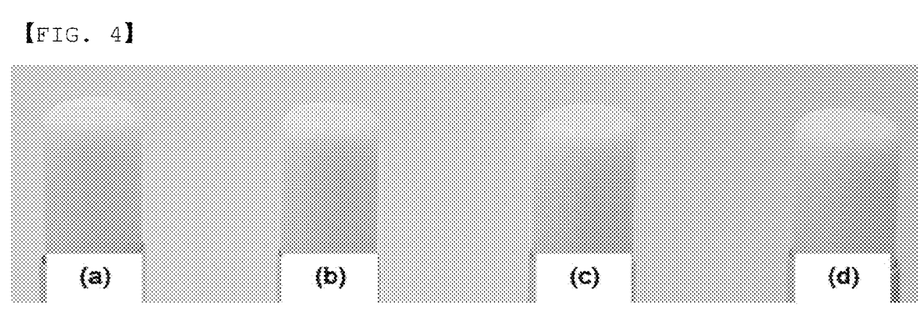
FIG. 4 shows the appearance of formulations including pigment capsule depending on the content of citric acid.

As shown in FIG. 4, when the content of Red 27 Lake was constant, the appearance color of the formulations did not significantly change even when the content of citric acid was increased.

Based on the results, it can be seen that when the content of citric acid reached a certain concentration level, the role of citric acid in color change was not significant.

Figure 5:
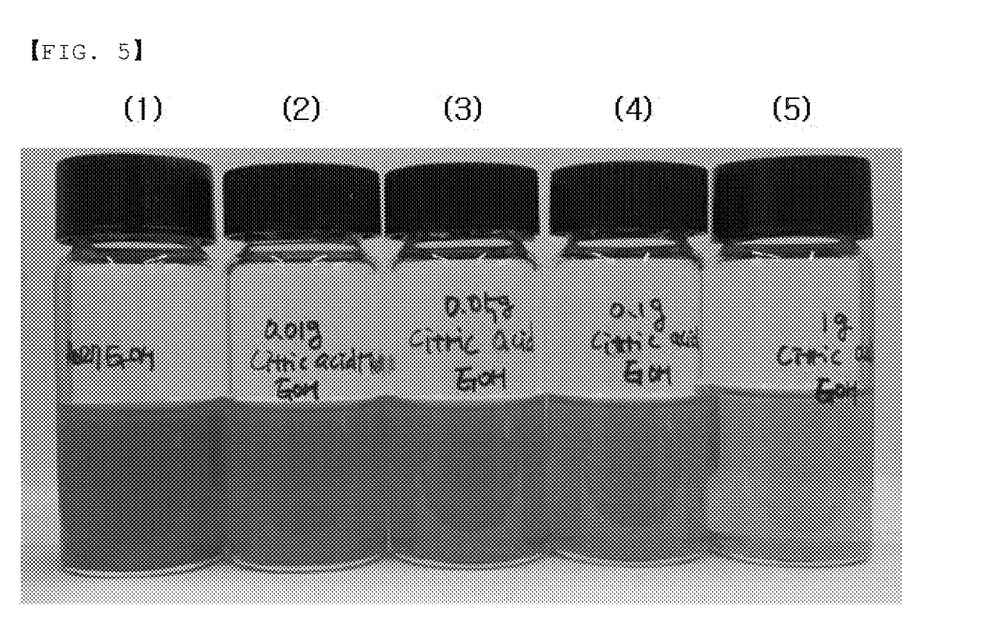
FIG. 5 shows the degree of color change of the pigment according to the content of citric acid ((1) ethanol only; (2) ethanol+0.01 g of citric acid; (3) ethanol+0.05 g of citric acid; (4) ethanol+0.1 g of citric acid; (5) ethanol+1 g of citric acid).

Meanwhile, in order to confirm the degree of color change by citric acid in the non-encapsulated pigments, 0.01 g of Red 27 Lake was dissolved in 10 ml of EtOH, and then 0 g, 0.01 g, 0.05 g, 0.1 g and 1 g of citric acid was added (corresponding to FIGS. 5 (1) to (5), respectively), and the color change of Red 27 Lake was observed. The results are shown in FIG. 5.

As shown in FIG. 5, it can be confirmed that when 0.01 g, 0.05 g and 0.1 g of citric acid was added, respectively, relative to the equivalent amount of Red 27 Lake, the color of Red 27 Lake appeared almost the same.

[Test Example 5] Observation of Appearance Color Development According to the Type of Oil in which the Pigment is Dispersed Pigment (Red 27 Lake) capsules or non-encapsulated pigments according to the present invention were dispersed in oil, and then the degree of pigment expression was observed according to the type of dispersion oil.

The appearance color of the case where an encapsulated pigment (1 g) or an unencapsulated dye (0.1 g) was dispersed in an alkylated polyvinylpyrrolidone/hexadecene copolymer (15 g), and the case where an encapsulated pigment (1 g) or a non-encapsulated pigment (0.1 g) was dispersed in a hydrogenated C6-14 olefin polymer (15 g) was observed. The results are shown in FIG. 6.

Figure 6:
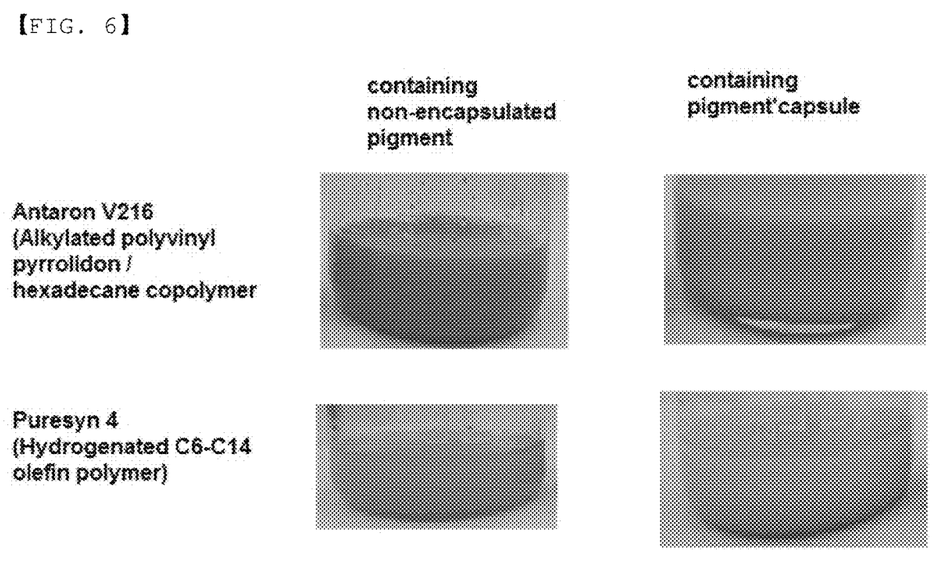
FIG. 6 shows the degree of expression of a pigment depending on the type of oils in which the pigment is dispersed.

Looking at FIG. 6, it can be confirmed that in the case of a non-encapsulated pigment, it shows a large difference in the coloring ability depending on the type of disperse oil, whereas in the case of the pigment capsule according to the present invention, it does not show a significant difference in the coloring ability depending on the type of the disperse oil.

[Experimental Example 6] Observation of Expression of Appearance Color of Formulations with and without Alumina The lipstick formulations containing pigment (Red 27 Lake) capsules or non-encapsulated pigments according to the present invention were prepared with the compositions of Table 7 below. At this time, when the pigment was dispersed in an oil phase consisting of wax and oil at 90 degrees for 5 minutes using an Agi mixer. When producing a matte lipstick, in order to determine the degree of color change of the formulation appearance depending on the presence or absence of alumina, which is a commonly used extender, the formulations C and D were configured to contain alumina in the dosage form.

TABLE 7

(unit: wt %)

| Raw material | Formulation A | Formulation B | Formulation C | Formulation D |
|---|---|---|---|---|
| Hydrogenated polyisobutene | 14 | 14 | 14 | 14 |
| Squalane | 14 | 14 | 14 | 14 |
| Caprylic/capric triglyceride | 10 | 10 | 10 | 10 |
| Polyethylene | 5 | 5 | 5 | 5 |
| Alkylated polyvinylpyrrolidone/ hexadecenecopolymer | — | — | — | — |
| Polyhydroxystearic acid | 0.5 | 0.5 | 0.5 | 0.5 |
| Titanium dioxide (CI 77891) | 0.6 | — | — | — |
| YELLOW 10 LAKE (CI 47005) | 0.05 | — | — | — |
| BLUE 1(CI 42090) | 0.015 | — | — | — |
| Alumina | — | — | 4 | 4 |
| Red 27 | 0.1 | — | 0.1 | — |
| Capsule | — | 1 | — | 1 |

Figure 7:
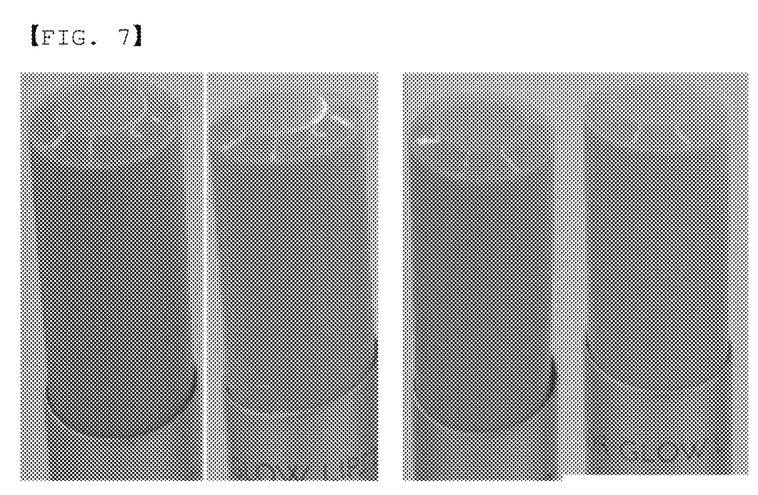
FIG. 7 shows the appearance of the formulation according to the presence or absence of alumina.

The appearance color of the lipstick formulation prepared with the above compositions is shown in FIG. 7.

Looking at FIG. 7, as compared with the case of containing a non-encapsulated pigment, the lipstick formulations containing the pigment capsules according to the present invention has a smaller change in appearance color than those using the non-encapsulated Red 27, irrespective of the type of additional ingredients. In particular, when a non-encapsulated pigment is contained, the appearance of the formulation shows more red color due to the addition of alumina, whereas in the case of containing the pigment capsule according to the present invention, the degree of change in appearance color of the formulation is remarkably small even when alumina is added.

[Test Example 7] Observation of Expression of Appearance Color and Coloring Ability on Skin with and without Red 27 in Formulation A lipstick formulation containing a pigment (Red 27 Lake) capsule according to the present invention (Formulation Example 1), a lipstick formulation containing a non-encapsulated Red 27 Lake (Comparative Formulation Example 1), and a lipstick formulation containing no pigment (Control group) were prepared with the composition shown in Table 8 below.

TABLE 8

|  | Formulation 1 | Formulation 2 | Formulation 3 |
|---|---|---|---|
| Polyethylene | 15.0 | 15.0 | 15.0 |
| Distearyl malate | 30.0 | 30.0 | 30.0 |
| Vaseline | 20.0 | 20.0 | 20.0 |
| Caprylic/capric triglyceride | 15.0 | 15.0 | 15.0 |
| RED 7 LAKE (CI 15850:1) | 2.0 | 2.0 | 2.0 |
| YELLOW 6 LAKE (CI 15985) | 3.5 | 3.5 | 3.5 |
| TITANIUM DIOXIDE (CI 77891) | 0.1 | 0.1 | 0.1 |
| IRON OXIDES (CI 77491) | 3.5 | 3.5 | 3.5 |
| Red 27 | — | — | 0.1 |
| Capsule | — | 1.0 | — |

The lipstick formulations prepared with the above compositions were applied to the skin of the back of the hand, and the degree of color development was observed. The results of the expression of exterior color and coloring ability on the skin of the polymer capsules are shown in FIG. 8.

Figure 8:
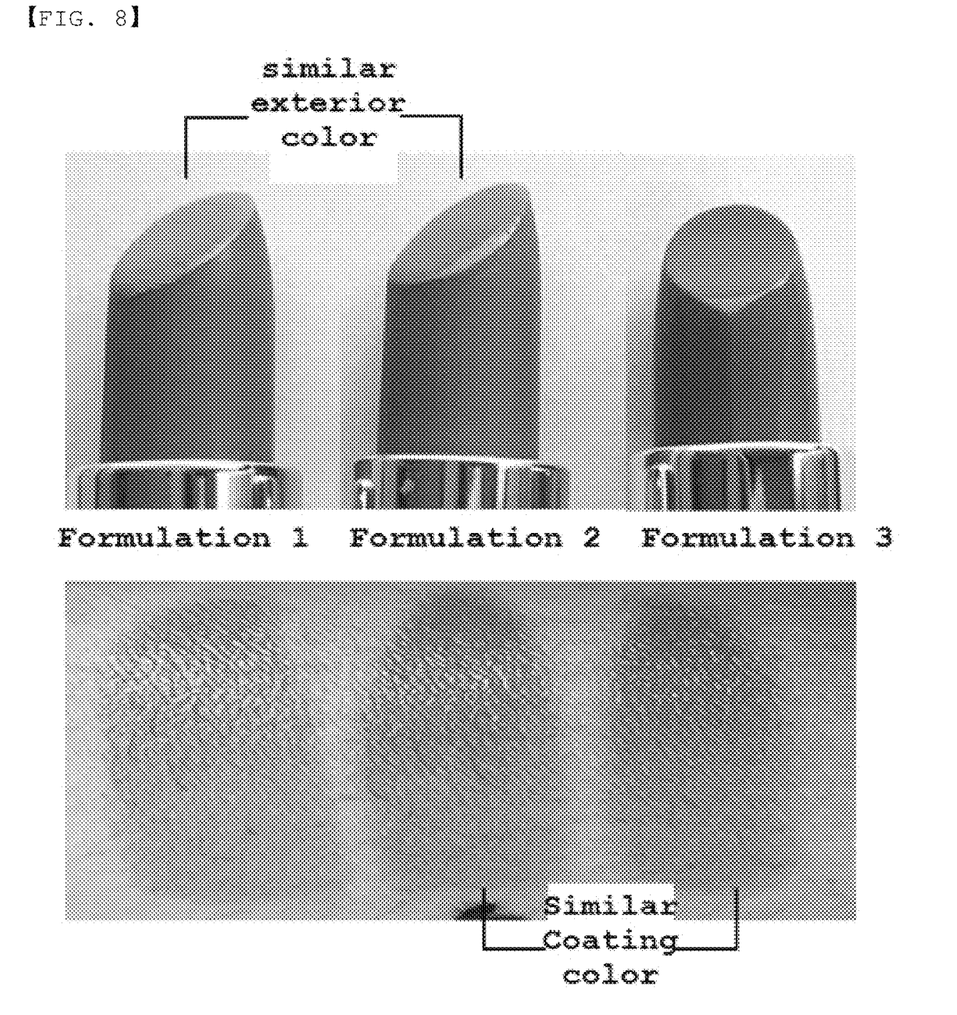
FIG. 8 shows the appearance of formulations containing pigment capsules or non-encapsulated pigments. The exterior color of lipstick in Formulation 2 does not appear to be reddish, but it appears reddish when applied to the skin.

Looking at FIG. 8, it can be confirmed that the formulation containing the encapsulated pigment according to the present invention (Formulation 2) showed an appearance color identical to that of the control lipstick containing no pigment (Formulation 1), and also showed excellent color developing ability on the skin identical to the formulation containing the non-capsulated Red 27 pigment (Formulation 3).

The invention claimed is:

1. A makeup cosmetic composition comprising a pigment capsule,
   wherein the capsule has an inner layer in which silica, a pigment, and a titanium dioxide pigment are dispersed, and an exterior covered with a polymer binder having a glass transition temperature of 130° C. or higher,
   wherein a $C_3$-$C_9$ trivalent carboxylic acid is contained in the inner layer of the makeup pigment capsule; and
   wherein the polymer binder is an acrylate copolymer the makeup cosmetic composition further includes one or more substance selected from the group consisting of polyhydroxy stearate, dipentaerythrityl tetrabehenate/ polyhydroxy stearate, dipentaerythrityl tri-polyhydroxystearate, ethylhexyl polyhydroxy stearate, iso-octyl polyhydroxystearate, and pentaerythrityl behenate/polyhydroxystearate, and a content of the one or more substance is 3 to 40% by weight based on the total weight of the makeup cosmetic composition.

2. The makeup cosmetic composition of claim 1, wherein a content of the pigment capsule is 0.01 to 30% by weight based on the total weight of the makeup cosmetic composition.

3. The makeup cosmetic composition of claim 1, wherein the makeup cosmetic composition is formulated into oil dispersion lipstick, oil dispersion liquid rouge, oil dispersion lip balm, oil dispersion lip gloss, oil dispersion lip palette, stick blusher, powder blusher, stick shadow, or powder shadow.

4. The makeup cosmetic composition of claim 1, wherein the pigment capsule has an average diameter of 10 μm to 15 μm.

* * * * *